(12) United States Patent
Chattopadhyay et al.

(10) Patent No.: US 11,169,062 B2
(45) Date of Patent: Nov. 9, 2021

(54) METHODS AND SYSTEMS FOR IDENTIFYING AN INTERNAL FLAW IN A PART PRODUCED USING ADDITIVE MANUFACTURING

(71) Applicant: The Boeing Company, Chicago, IL (US)

(72) Inventors: Aditya Chattopadhyay, Chicago, IL (US); Melissa Garner, Chicago, IL (US); Calvin Brown, Chicago, IL (US); Christine Sauerbrunn, Chicago, IL (US)

(73) Assignee: The Boeing Company, Chicago, IL (US)

( * ) Notice: Subject to any disclaimer, the term of this patent is extended or adjusted under 35 U.S.C. 154(b) by 277 days.

(21) Appl. No.: 16/125,670

(22) Filed: Sep. 8, 2018

(65) Prior Publication Data
US 2020/0080920 A1 Mar. 12, 2020

(51) Int. Cl.
*G01N 3/06* (2006.01)
*G01N 3/08* (2006.01)

(52) U.S. Cl.
CPC ............. *G01N 3/066* (2013.01); *G01N 3/08* (2013.01)

(58) Field of Classification Search
CPC . G01M 7/02; G01B 7/14; B33Y 50/00; B06B 1/06; G01J 5/48; G01N 3/32; G01N 3/06; G01N 33/2045
See application file for complete search history.

(56) References Cited

U.S. PATENT DOCUMENTS

| | | | | |
|---|---|---|---|---|
| 10,663,370 | B2* | 5/2020 | De Baere | G01M 3/26 |
| 2006/0201577 | A1* | 9/2006 | King | G01N 3/12 141/83 |
| 2016/0237804 | A1* | 8/2016 | Papadimitriou | E21B 47/007 |
| 2017/0097280 | A1* | 4/2017 | Drescher | G01M 7/022 |

(Continued)

OTHER PUBLICATIONS

25th Design Conference Innovative Product Creation, 2015, G. Moroni, W Syam, S. Petro, "Functionality-based part orientation for additive manufacturing", pp. 217-222, [online] [retrieved on Jul. 28, 2020] retrieved from <https://www.sciencedirect.com> (Year: 2015).*

(Continued)

*Primary Examiner* — Eman A Alkafawi
*Assistant Examiner* — Denise R Karavias
(74) *Attorney, Agent, or Firm* — McDonnell Boehnen Hulbert & Berghoff LLP

(57) ABSTRACT

An example method for identifying an internal flaw in a part produced using additive manufacturing includes calculating a proof load of a part, in which the proof load is a load that when applied to the part will cause the part to fail based on presence of an internal flaw in the part, determining whether the part can withstand the proof load based on a geometry of the part and static strength data, and based on a determination that the part can withstand the proof load, applying the proof load to the part during a compliance test of the part. The proof load causes the part to fracture, when applied to the part, based on presence of the internal flaw in the part that is of a threshold size at which the internal flaw would cause cracking and potential part failure when the part is placed under the operational load.

20 Claims, 8 Drawing Sheets

(56) References Cited

U.S. PATENT DOCUMENTS

2017/0232517 A1* 8/2017 Morton .................. G06F 30/23
 419/29
2018/0318922 A1* 11/2018 Valls Angles ............. B22F 3/10

OTHER PUBLICATIONS

MechaniCalc, Inc. "Fracture Mechanics", Jul. 30, 2018, [online] [retrieved on 07-329-2020] retrieved from internet <https://web.archive.org/web/20180730020800/https://mechanicalc.com/reference/fracture-mechanics> (Year: 2018).*

Rankouhi et al., "Failure Analysis and Mechanical Characterization of 3D Printed ABS with Respect to Layer Thickness and Orientation", Journal of Failure Analysis and Prevention, vol. 16, No. 3, May 3, 2016, pp. 467-481 (Year: 2016).*

Wycisk et al., "Effects of Defects in Laser Additive Manufactured Ti-6A1-4V on Fatigue Properties", Physics Procedia, vol. 56, No. 9, Sep. 9, 2014, pp. 371-378 (Year: 2014).*

AMS 2175 Revision A, "Castings, Classification and Inspection of," SAE Aerospace (Jul. 2010.).

F. Cao, K.S. Ravi Chandran, "The role of crack origin size and early stage crack growth on high cycle fatigue of powder metallurgy Ti—6Al—4V alloy," International Journal of Fatigue (May 2017), 48-58.

H. Gong, K. Rafi, T. Starr, B. Stucker, "Effects of defects on fatigue tests of as-built Ti—6Al—4V parts fabricated by selective laser melting," Solid Freeform Fabrication Symposium (Aug. 2012), 499-506.

D. Eylon, "Fatigue crack initiation in hot isostatically pressed Ti—6Al—4V castings," Journal of Material Science (Aug. 1979), 1914-22.

S. Leuders, S. Meiners, L. Wu, A. Taube, T. Troster, T. Niendorf, "Structural components manufactured by Selective Laser Melting and Investment Casting-Impact of the process route on the damage mechanism under cyclic loading," Journal of Material Processing Technology (May 2017), 130-142.

P. Edwards, M. Ramulu, "Effects of build direction on the fracture toughness and fatigue crack growth in selective laser melted Ti—6Al—4V," Fatigue & Fracture of Engineering Material & Structures (Mar. 2015), 1228-1236.

M. Kahlin, H. Ansell, J.J. Moverare, "Fatigue behavior of additive manufactured Ti6Al4V, with as-built surfaces, exposed to variable amplitude loading," International Journal of Fatigue (Jun. 2017), 353-362.

MMPDS-10, "Metallic Materials Properties Development and Standardization," Battelle Memorial Institute (2015).

E.F. Bruhn, "Section D Connections and Design Details," Analysis & Design of Flight Vehicle Structures, 1973 edition/(1973), D1.1-D3.16.

R.C. Hibbeler, "Chapter 8: Combined Loadings," Mechanics of Materials, 8th ed. (2005), 405-436.

Rankouhi et al., "Failure Analysis and Mechanical Characterization of 3D Printed ABS with Respect to Layer Thickness and Orientation", Journal of Failure Analysis and Prevention, vol. 16, No. 3, May 3, 2016, pp. 467-481.

Wycisk et al., "Effects of Defects in Laser Additive Manufactured Ti-6A1-4V on Fatigue Properties", Physics Procedia, vol. 56, No. 9, Sep. 9, 2014, pp. 371-378.

Extended European Search Report prepared by the European Patent Office in Application No. EP 19 18 2671.8 dated Dec. 17, 2019.

T.L. Anderson, "10.9 Fatigue Crack Growth Experiments," Fracture Mechanics: Fundamentals and Applications, 4th ed. (2017), 521-527.

* cited by examiner

PERFORMING ONE OR MORE TESTS TO OBTAIN THE CRITICAL FRACTURE TOUGHNESS AND THE THRESHOLD STRESS-INTENSITY FACTOR OF THE MATERIAL FOR THE PART IN X, Y, AND Z DIRECTIONS — 228

FIG. 18

IDENTIFYING THE STATIC STRENGTH DATA INCLUDING TENSILE STRENGTH ($F_{TU}$), YIELD STRENGTH ($F_{TY}$), YIELD BEARING STRENGTH ($F_{BRU}$), AND PERCENT ELONGATION OF THE MATERIAL OF THE PART — 230 — 204

FIG. 19

PERFORMING A SIMULATION RESULTING IN A BINARY DECISION — 232 — 204

FIG. 20

CALCULATING A MATERIAL RATIO OF THE PART AS THE CRITICAL FRACTURE TOUGHNESS OVER THE THRESHOLD STRESS-INTENSITY FACTOR — 234

CALCULATING A LOAD RATIO OF THE PART AS A LIMIT LOAD ON THE PART OVER THE OPERATIONAL LOAD — 236

BASED ON THE LOAD RATIO BEING GREATER THAN THE MATERIAL RATIO, APPLYING THE PROOF LOAD TO THE PART — 238

FIG. 21

DETERMINING A THICKNESS OF A FATIGUE-CRITICAL SECTION OF THE PART — 240

BASED ON THE THICKNESS OF A FATIGUE-CRITICAL SECTION OF THE PART BEING LESS THAN A THRESHOLD THICKNESS, APPLYING THE PROOF LOAD TO THE PART — 242

FIG. 22

USING A NON-DESTRUCTIVE INSPECTION METHOD DURING THE COMPLIANCE TEST OF THE PART — 244

FIG. 23

METHODS AND SYSTEMS FOR IDENTIFYING AN INTERNAL FLAW IN A PART PRODUCED USING ADDITIVE MANUFACTURING

STATEMENT REGARDING FEDERALLY SPONSORED RESEARCH OR DEVELOPMENT

This invention was made with Government support under FA8650-16-2-5700 awarded by the United States Air Force. The Government has certain rights in this invention.

FIELD

The present disclosure relates to a method for identifying an internal flaw in a part produced using additive manufacturing, and more particularly, to determining a proof load that will cause a part to fracture if a flaw large enough to grow under operational load exists in the part.

BACKGROUND

A concern with metal parts produced using additive manufacturing (e.g., 3D printing) is that the metal parts may contain internal flaws that are hard to detect and/or are not visible to inspectors, especially if surfaces of the metal parts are left in the as-printed condition.

Existing solutions for validating a part after production include use of a radiographic inspection. Radiographic inspection is performed using a radioactive isotope or an x-ray tube to create an image on a film or in a digital format. This non-destructive testing (NDT) method is a volumetric inspection in which defects that are not open to a surface can be detected that may not otherwise be detectable. A vast array of material and products can be examined for discontinuities using radiographic inspection, ranging from tiny electronic components to large vessels.

However, for additive manufactured parts, radiographic inspection may be difficult to perform in certain cases as a rough as-printed surface finish of an additive manufactured metal part can obscure any internal flaws that may exist in the part.

What is needed is a method for validating additive manufactured parts to help ensure that the parts will not crack due to fatigue loading over the part's service life. This would address a concern of difficult-to-detect internal flaws.

SUMMARY

In an example, a method for identifying an internal flaw in a part produced using additive manufacturing is described. The method comprises calculating a proof load of a part, and the proof load is a load that when applied to the part will cause the part to fail based on presence of an internal flaw in the part. The proof load is dependent upon an operational load for the part and stress intensity data for a material of the part. The method also comprises determining whether the part can withstand the proof load based on a geometry of the part and static strength data, and based on a determination that the part can withstand the proof load, applying the proof load to the part during a compliance test of the part. The proof load causes the part to fracture, when applied to the part, based on presence of the internal flaw in the part that is of a threshold size at which the internal flaw would cause cracking and potential part failure when the part is placed under the operational load.

In another example, a system for identifying an internal flaw in a part produced using additive manufacturing is described. The system comprises one or more processors, and a non-transitory computer readable storage medium having stored therein instructions, that when executed by the one or more processors, causes the one or more processors to perform functions. The functions comprise calculating a proof load of a part, and the proof load is a load that when applied to the part will cause the part to fail based on presence of an internal flaw in the part. The proof load is dependent upon an operational load for the part and stress intensity data for a material of the part. The functions also comprise determining whether the part can withstand the proof load based on a geometry of the part and static strength data, and based on a determination that the part can withstand the proof load, causing the proof load to be applied to the part during a compliance test of the part. The proof load causes the part to fracture, when applied to the part, based on presence of the internal flaw in the part that is of a threshold size at which the internal flaw would cause cracking and potential part failure when the part is placed under the operational load.

In another example, a non-transitory computer readable storage medium is described having stored therein instructions, that when executed by a system having one or more processors, causes the system to perform functions. The functions comprise calculating a proof load of a part produced using additive manufacturing, and the proof load is a load that when applied to the part will cause the part to fail based on presence of an internal flaw in the part. The proof load is dependent upon an operational load for the part and stress intensity data for a material of the part. The functions also comprise determining whether the part can withstand the proof load based on a geometry of the part and static strength data, and based on a determination that the part can withstand the proof load, causing the proof load to be applied to the part during a compliance test of the part. The proof load causes the part to fracture, when applied to the part, based on presence of the internal flaw in the part that is of a threshold size at which the internal flaw would cause cracking and potential part failure when the part is placed under the operational load.

The features, functions, and advantages that have been discussed can be achieved independently in various examples or may be combined in yet other examples. Further details of the examples can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings which are not necessarily drawn to scale, wherein:

FIG. 18 shows a flowchart of an example method for use with the method of FIG. 10, according to an example implementation.

FIG. 19 shows a flowchart of an example method for determining whether the part can withstand the proof load of FIG. 10, according to an example implementation.

FIG. 20 shows another flowchart of an example method for determining whether the part can withstand the proof load of FIG. 10, according to an example implementation.

FIG. 21 shows another flowchart of an example method for use with the method of FIG. 10, according to an example implementation.

FIG. 22 shows another flowchart of an example method for use with the method of FIG. 10, according to an example implementation.

FIG. 23 shows another flowchart of an example method for use with the method of FIG. 10, according to an example implementation.

DETAILED DESCRIPTION

Figure 1:
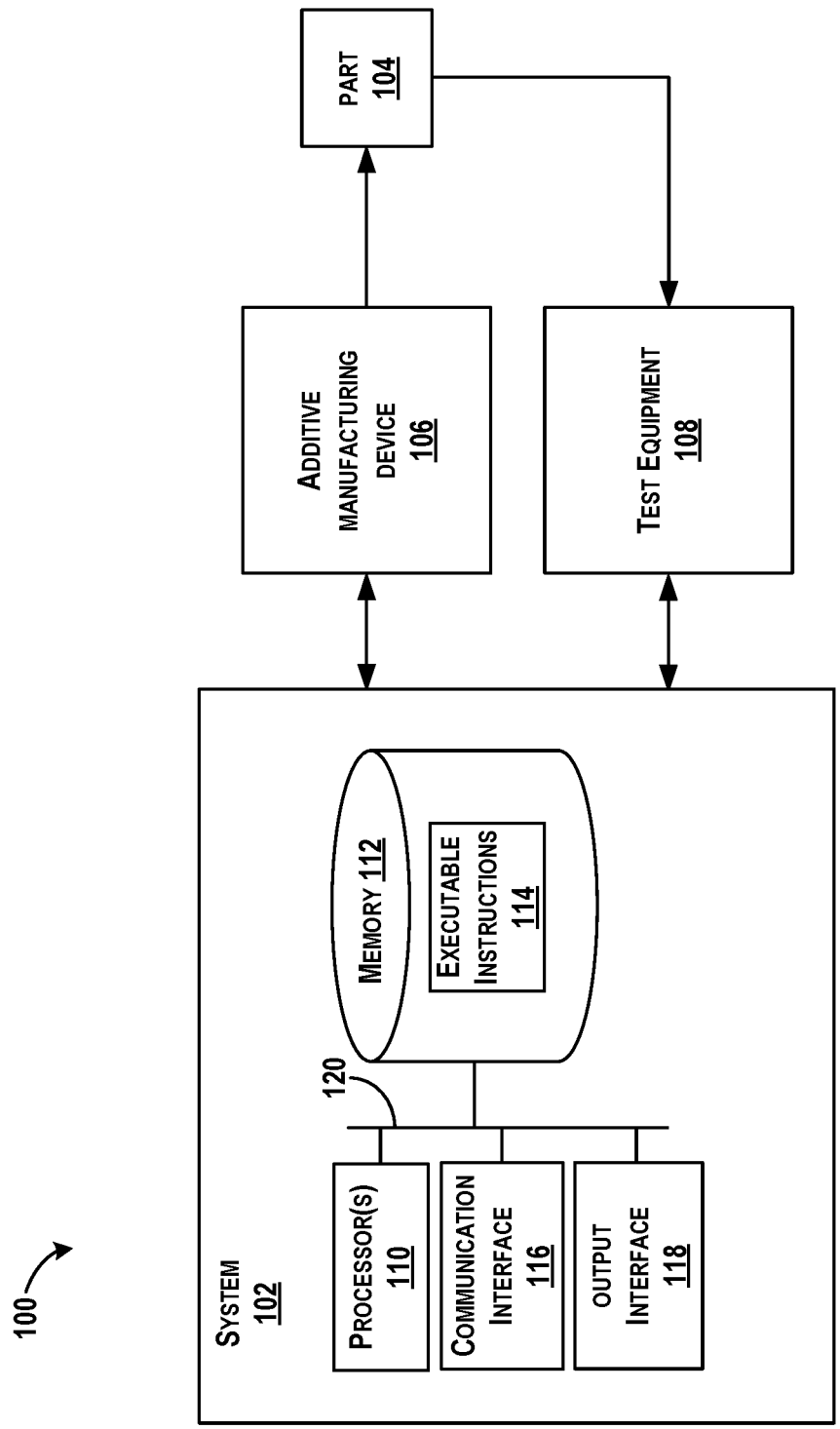
FIG. 1 illustrates a work environment, according to an example implementation.

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

Many vehicles or machinery in use today have been operated beyond their original design service lives. This leads to issues in procuring spare or replacement parts for the items. When a part fails, an original manufacturer may no longer be available, or may be unwilling to produce a small run of difficult-to-manufacture parts. This problem is particularly pronounced for castings, which require significant time and resources to set up tooling required for a production run.

Metal additive manufacturing (AM) provides an alternative to casting for manufacturing geometrically-complicated metal components, for example, to enable replacement parts to be produced more quickly and easily. Parts produced using additive manufacturing provide strength comparable to castings, but do not have as significant tooling requirements as castings.

When replacing a casting part with an additive manufactured part in certain industries (e.g., aerospace applications), qualification of the part for use is required. For example, some regulations define an acceptable number and size of flaws in a casting for a given strength class. An analogous specification for parts produced using additive manufacturing techniques is not openly available, however. In addition, using traditional non-destructive inspection techniques to qualify an additive manufactured part can be difficult, such as for example, if a rough surface finish of any areas of the part remain in an as-printed condition which can make a detection of internal flaws using radiographic inspection in a metal additive manufactured part difficult as compared to a part produced with casting.

Additive manufactured parts can thus be qualified for their static load requirements by performing limit and ultimate testing instead of (or in addition) to non-destructive inspection techniques. However, a question arises concerning a fatigue strength of an additive manufactured part because it can be difficult to demonstrate that an additive manufactured part has sufficient fatigue strength for the particular use case when an original casting was not subject to fatigue analysis or limit testing in the first place.

Example methods and systems described herein include features for ensuring that additive manufactured parts meet fatigue requirements through an application of a proof load during an Acceptance Test Procedure (ATP) of the part. Additive manufactured parts may contain internal flaws that are not visible to inspectors and may not be found with existing scanning techniques. However, limit or proof load testing can validate a part for use when a proper proof load is used. The proof load is a load that will cause a part to fracture if a flaw (e.g., internal flaw) large enough to grow under operational load exists in the part. Such testing addresses a concern of difficult-to-detect internal flaws in additive manufactured parts.

In examples, the proof load for the additive manufactured part is dependent on the operational load, fracture toughness, and threshold stress-intensity factor of the part. For example, a proof strength of a part (e.g., stress level above which an internal flaw will result in a crack) is calculated and applied to the part. Because the proof load is greater than a fatigue load, any flaw that would result in a crack as a result of fatigue will present itself when subjected to the proof load.

Any part that passes the ATP would therefore be considered safe to use over its service life. Thus, example testing methods and systems described herein may identify any additive manufactured part that includes a critical flaw. The methods and systems described herein of ensuring that no critical flaws exist in a part may be applicable to mechanisms subject to high ultimate loads but relatively low operational loading, such as flight controls and high-lift actuator housings in aircraft, for instance.

Referring now to the figures, FIG. 1 illustrates a work environment 100, according to an example implementation. The work environment 100 includes a system 102 system for identifying an internal flaw in a part 104 produced using additive manufacturing. The system 102 is coupled to an additive manufacturing device 106 and test equipment 108.

The system 102 may either be directly or indirectly coupled to the additive manufacturing device 106 and the test equipment 108, such as by using wireless or wired means. The system 102 may be used to perform functions of methods described herein. The system 102 may take the form of a computing device, for example, and includes one or more processors 110, a memory 112 (e.g., a non-transitory computer readable storage medium) having stored therein executable instructions 114, that when executed by the processor(s) 110, causes the processor(s) 110 to perform functions for identifying an internal flaw in the part 104. The system 102 is also shown to include a communication interface 116 and an output interface 118, and all components of the system 102 are each connected to a communication bus 120. The system 102 may also include hardware to enable communication within the system 102 and between the system 102 and other devices (not shown). The hardware may include transmitters, receivers, and antennas, for example.

The communication interface 116 may be a wireless interface and/or one or more wireline interfaces. The communication interface 116 allows for both short-range communication and long-range communication to one or more networks or to one or more remote devices.

The memory 112 may include or take the form of one or more computer-readable memory or computer readable storage media that can be read or accessed by the processor(s) 110. The computer-readable storage media can include volatile and/or non-volatile storage components, such as optical, magnetic, organic or other memory or disc storage, which can be integrated in whole or in part with the processor(s) 110. The memory 112 is considered non-transitory computer readable memory or non-transitory computer readable media. In some examples, the memory 112 can be implemented using a single physical device (e.g., one optical, magnetic, organic or other memory or disc storage unit), while in other examples, the memory 112 can be implemented using two or more physical devices.

The memory 112 thus is a non-transitory computer readable memory, and the executable instructions 114 are stored thereon. The instructions 114 include computer executable code. When the instructions 114 are executed by the processor(s) 110, the processor(s) 110 are caused to perform functions of the system 102.

The processor(s) 110 may be a general-purpose processor or a special purpose processor (e.g., digital signal processors, application specific integrated circuits, etc.). The processor(s) 110 may receive inputs from the communication interface 116 as well as from the additive manufacturing device 106 and the test equipment 108, and process the inputs to generate outputs that are stored in the memory 112 and output via the output interface 118, such as to send the outputs to the additive manufacturing device 106 and/or the test equipment 108.

Thus, the output interface 118 outputs information to the additive manufacturing device 106 and/or the test equipment 108 or to other components as well. Thus, the output interface 118 may be similar to the communication interface 116 and can be a wireless interface (e.g., transmitter) or a wired interface as well.

As mentioned, the memory 112 has stored therein executable instructions 114, that when executed by the processor(s) 110, causes the processor(s) 110 to perform functions for identifying an internal flaw in the part 104. In some examples, to achieve this operation, functions include calculating a proof load of the part 104, determining whether the part 104 can withstand the proof load based on a geometry of the 104 part and static strength data, and based on a determination that the part 104 can withstand the proof load, causing the proof load to be applied to the part 104 during a compliance test of the part 104. The proof load is a load that when applied to the part 104 will cause the part to fail based on presence of an internal flaw in the part 104, and the proof load is dependent upon an operational load for the part 104 and stress intensity data for a material of the part 104. The proof load causes the part 104 to fracture, when applied to the part 104, based on presence of the internal flaw in the part 104 that is of a threshold size at which the internal flaw would cause cracking and potential part failure when the part 104 is placed under the operational load. The system 102 causes the proof load to be applied to the part 104 through operation and/or control of the test equipment 108.

The part 104 is an additively manufactured part, and may take any form, such as a part for an aircraft, an aircraft flight control system part, a bellcrank in a flight control system, or other aircraft part.

The additive manufacturing device 106 can produce three-dimensional parts layer by layer from a material, such as a polymer or metal based material. The additive manufacturing device 106 may receive a digital data file from the system 102 that includes details of the part 104 to be produced. The additive manufacturing device 106 using an additive process rather than a subtractive process that removes layers of material, such as milling. The additive manufacturing device 106 may include many components, such as a printing head, control mechanisms (e.g., computing device), molds, etc., depending on a type of manufacturing being used. A range of processes finding industrial applications for additive manufacturing includes direct metal deposition, electron beam melting, polymer processes such as fused filament fabrication (FFF), fused deposition (FDM), Solid Ground Curing (SGC), Laminated Object Manufacturing (LOM), and select laser sintering (SLS) or selective laser melting (SLM), among others. The additive manufacturing device 106 may include components specific to any of these processes, or in some examples, the additive manufacturing device 106 may include hybrid machine tools to combine additive manufacturing with subtractive machining.

The additive manufacturing device 106 may use a variety of materials to produce the part 104, such as stainless steels, aluminum, nickel, cobalt-chrome, titanium alloys, copper alloys, precious metal alloys, nickel based alloys, aluminum alloys, and cobalt based alloys.

In some examples, to achieve necessary specifications or improve properties such as surface quality, geometrical accuracy and mechanical properties, it is often necessary to post-process and finish parts produced with the additive manufacturing device 106. A surface roughness for the part 104 can be enhanced by adding fabrication processes to the process chain. A high quality of metal products produced using additive manufacturing processes enables the use of many metal-machining finishes to meet requirements of surface quality and geometry. Following removal of support structures to separate the part 104 from a build platform, the part 104 can be milled, drilled, polished, etc. Internal surfaces, such as those in internal/tempering channels for example, can be polished using abrasive flow machining. Heat treatment is often included in a process chain as well as shot peening to improve mechanical and tactile properties of the surface of the part 104. Another post process that can be used is electro-polishing to improve a surface finish of the part 104.

Once the part 104 has been produced and the proof load has been calculated, the test equipment 108 is controlled and/or operated by the system 102 to apply the proof load to the part 104 during a compliance test of the part 104. The test equipment 108 may take many forms depending on a size of the part, for example. One example of the test equipment 108 includes a tensile machine that can exert a vertical force on the part 104, and can measure the force applied to the part 104 as the part 104 holds, distends, or breaks depending on the test.

As mentioned, it may be necessary to test the part 104 for fatigue cracks in the part 104, which can initiate from a free surface or from internal flaws. As a point of comparison, for parts produced through casting, a greater level of inhomogeneity in a microstructure of the part in comparison to a wrought alloy can result in a number of cycles at which a transition from surface-to-internal crack initiation occurs to decrease by an order of magnitude. As an example, a comparison between printed Ti-6Al-4V (Titanium-Aluminum-Vanadium) parts showed that including small internal defects in a test specimen caused it to fail from these internal defects in 62.5% of the trials. Removal of defects would be useful in improving fatigue life of the part. However, research on Ti-6Al-4V castings has shown that even after hot isostatic pressing (HIP) and healing all of the casting defects, large grain sizes and α-platelet colonies act as large initial cracks. Castings are micro-structurally similar to additive printed metal parts, so this issue should be considered.

Parts produced using additive manufacturing (e.g., selective laser melting (SLM)) techniques are built up by laying down a layer of powder and sintering a component layer-by-layer. This process provides properties comparable to that of a casting. Static properties in a printed metal part are generally superior to those in a casting, but high-cycle fatigue properties are typically lower. An improvement in the static strength of a part that is produced using additive manufacturing does not therefore correspond with an increase in its fatigue performance.

It is also be noted that many methods exist by which metals can be additively manufactured. Some methods used in aerospace include the SLM method, mentioned previously, as well as electron beam melting (EBM). Comparison between Ti-6Al-4V parts produced using SLM and EBM methods have indicated that SLM parts tend to show better fatigue lives in comparison to parts produced using EBM, though both are outperformed by wrought material. In addition, performing a HIP post-processing operation on the AM components was not found to significantly change the fatigue life of a component subject to variable-amplitude fatigue spectra.

Thus, existence of internal flaws and variation in strength, fracture toughness, and fatigue life that results from an anisotropic nature of the part 104 can make fatigue life assessments difficult. Example systems and methods described herein enable identifying an internal flaw in the part 104 produced using additive manufacturing. The methods utilize proof load testing of the part 104.

Figure 2:
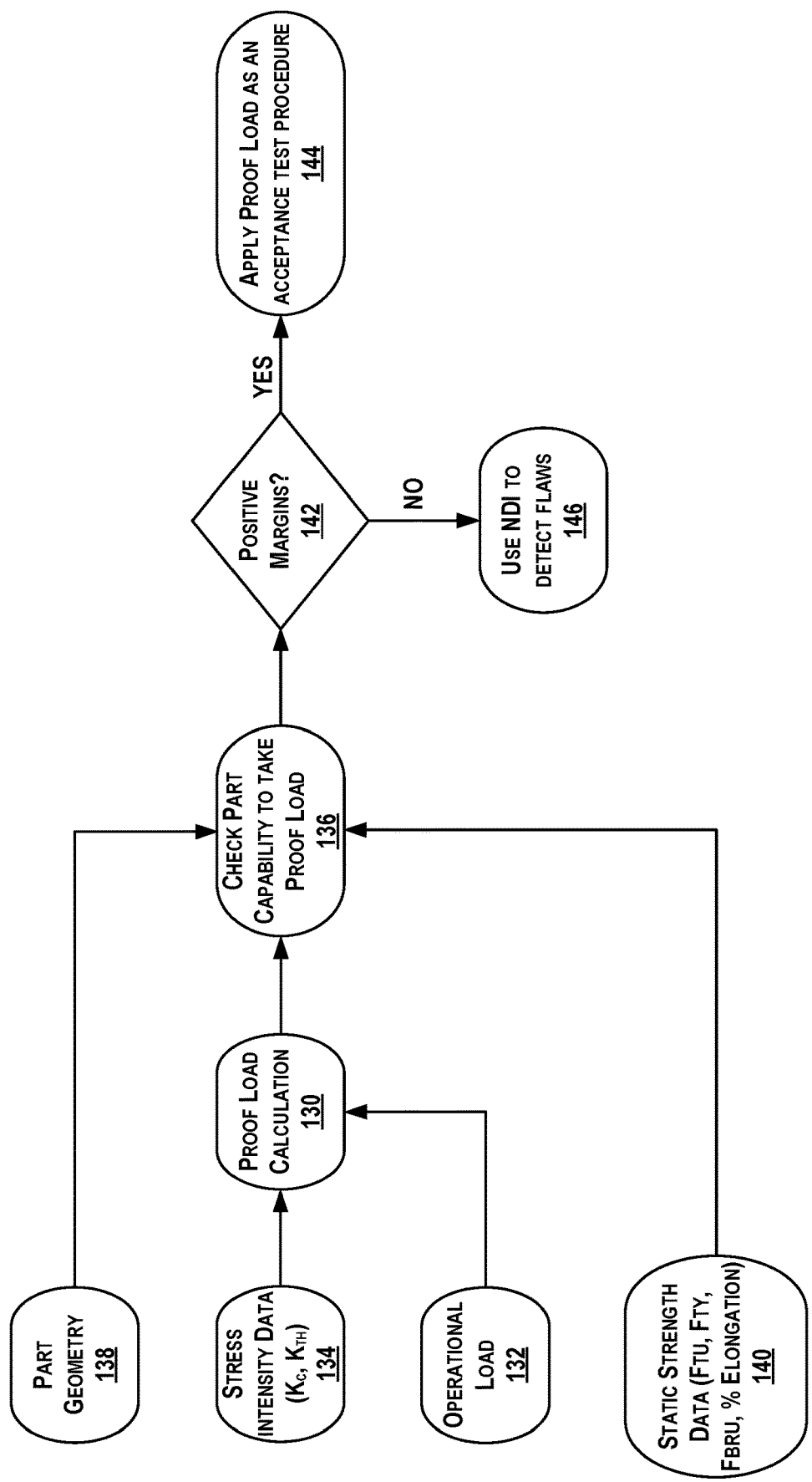
FIG. 2 is a flow diagram illustrating an example test procedure, according to example implementations described herein.

FIG. 2 is a flow diagram illustrating an example test procedure, according to example implementations described herein. A first step for the process of identifying an internal flaw in the part 104 includes calculating a proof load of the part 104, as shown at 130. The proof load is a load that when applied to the part 104 will cause the part to fail based on presence of an internal flaw in the part 104. The proof load is greater than the operational load of the part 104, so that if the part 104 withstands the proof load, the part 104 will be capable of withstanding operational loads when put in use.

The part 104 may not immediately fracture when placed under operational load if left with an internal flaw of the threshold size. However, it would not be desirable to place a part into use that has such a flaw. Thus, using a proof load larger than the operational load enables a flaw of the threshold size to cause the part 104 to fracture under the proof load, which such flaw could cause immediate failure or could only propagate cracking under operational load and could eventually cause the part 104 to fail.

As a result, calculating of a proof load determines a load to apply that will ensure that no crack or flaw exists in the part 104 that might grow when subject to operational loads. Traditionally, a proof load is simply applied as 1.5 times a limit load or highest load expected to be experienced by the part in service. However, within examples described herein, the proof load is greater than 1.5 times the limit load, and is calculated to be specific for the part and based on material fracture toughness of the material used to produce the part. Specifically, a magnitude of the proof load was found to be dependent on an operational load for the part 104 and stress intensity data for a material of the part 104, as shown at blocks 132 and 134 in FIG. 2.

Within examples, the stress intensity data for the material of the part 104 includes a critical fracture toughness ($K_c$) and a threshold stress-intensity factor ($K_{th}$) of the material for the part 104. The critical fracture toughness ($K_c$) may be based on a print direction of the part 104 during the additive manufacturing of the part 104. For example, an influence of layer-by-layer creation of a printed metal part can be considered when analyzing its fatigue performance. A fracture toughness of a printed Ti-6Al-4V sample, for example, with a crack-front parallel to a printer bed (loading in a print direction) was found to have a fracture toughness of less than 60% compared to a crack-front moving perpendicular to the printer bed (loading perpendicular to the print direction). However, a threshold stress-intensity factor ($K_{th}$) of the printed material did not vary significantly with respect to the print direction. The result that the print direction affects the fracture toughness of a printed part but not the threshold stress-intensity factor is of particular interest, as it can be leveraged to reduce a required proof load on a part if the print direction can be specified, the geometry is appropriate, and if the loading direction does not vary much under operational conditions.

As such, the proof load can thus be calculated as follows:

$$P_{proof} = \left(\frac{K_c}{K_{th}}\right) P_{fat} \qquad \text{Equation (1)}$$

where:

$P_{proof}$ is a load that will fracture the part 104 if a crack large enough to grow at operational load exists in the part 104;

$K_c$ is a critical fracture toughness (e.g., a critical stress intensity factor of the part 104);

$K_{th}$ is a threshold stress-intensity factor; and $P_{fat}$ is an operational load on the part 104.

Thus, the proof load is calculated based on a ratio of the critical fracture toughness and the threshold stress-intensity factor.

The proof load calculation is determined through an analysis of a size of a crack that will not grow under operational load, which can be estimated using a threshold stress-intensity factor for a material. The stress intensity factor for a crack is given by the expression below:

$$K = S(\pi * a)^{0.5} Y \quad \text{Equation (2)}$$

where:

K is the stress intensity factor, typically with units of ksi*in^0.5;

S is a remote stress in a cracked section;

a is a crack length; and

Y is a geometry factor.

The threshold stress-intensity factor is a stress intensity below which a crack will not grow. If the threshold stress-intensity factor, $K_{th}$, and operational stress, $S_{fat}$, are substituted into Equation (2), a size of crack that will not grow for a given geometry, material, and stress level can be obtained:

$$K_{th} = S_{fat}(\pi * a_{no\ grow})^{0.5} Y \quad \text{Equation (3)}$$

Equation (3) can be rearranged for $a_{no\ grow}$, which is a length of crack that will not grow for a given structure and operational stress as follows:

$$a_{no\ grow} = \left(\frac{1}{\pi}\right)\left(\frac{K_{th}}{S_{fat}Y}\right)^2 \quad \text{Equation (4)}$$

where:

$a_{no\ grow}$ is a size of crack that will not grow for a given part and stress level;

$K_{th}$ is the threshold stress-intensity factor of the material of the part;

$S_{fat}$ is a remote stress resulting from operational load application; and

Y is the geometry factor.

The stress level required to fracture a part that contains a crack of length $a_{no\ grow}$ can now be obtained by inputting the critical stress intensity factor, $K_c$, into Equation (3) with a crack length of $a_{no\ grow}$ and solving for a required stress level:

$$K_c = S_{proof}(\pi * a_{no\ grow})^{0.5} Y \quad \text{Equation (5)}$$

The stress required to fracture the part, $S_{proof}$, can be isolated in the above expression as follows:

$$S_{proof} = \frac{K_c}{((\pi * a_{no\ grow})^{0.5} Y)} \quad \text{Equation (6)}$$

The crack length $a_{no\ grow}$ may be expressed in terms of threshold stress-intensity factor, operational stress, and the geometry factor, and substituted into Equation (6) as follows:

$$S_{proof} = \frac{K_c}{\left(\left(\pi\left(\frac{1}{\pi}\right)\left(\frac{K_{TH}}{S_{fat}Y}\right)^2\right)^{0.5} * Y\right)} \quad \text{Equation (7)}$$

The expression for $S_{proof}$ simplifies to the form shown below:

$$S_{proof} = \left(\frac{K_c}{K_{th}}\right) S_{fat} \quad \text{Equation (8)}$$

Since the proof and operational stress are a function of the same geometry, the proof and operational loads can be related as shown in Equation (1) above.

Using the example proof load calculation enables proofing of the part 104 for an acceptance test procedure, as it ensures that the part 104 does not contain a flaw large enough to grow under operational loads. The example method requires that the threshold stress-intensity factor, critical fracture toughness, and operational load on the part 104 are known. The operational load on the part 104 can be obtained through looking at usage of the system in which the prior metal (casted) part was a component (e.g., looking at how prior parts operated to obtain the operational load). The threshold stress intensity factor and critical fracture toughness of the part 104 can be obtained through testing specimens of the printed material in a z (print) and x-y directions. Standard methods of testing the specimens can be used, such as using a tensile testing machine to pull the specimen from both ends and measure a force required to pull the specimen apart and how much the sample stretches before breaking (e.g., ability to resist breaking under tensile stress and maximum elongation of a material in length that occurs before it breaks under tension).

After calculation of the proof load, the test procedure shown in FIG. 2 next determine whether the part 104 can withstand the proof load based on a geometry of the part (e.g., determined from the 3D printed data file) and static strength data to check part capability to take the proof load, as shown at blocks 136, 138, and 140. For example, it may be beneficial to cross-check the proof load found to ensure that the proof load will not statically overload the part 104 upon load application. This can be performed using the static strength data, such as Ftu (e.g., first mechanical property or ultimate tensile strength), Fty (e.g., yield strength), Fbru (e.g., yield bearing strength), and percent elongation (e.g., % elongation or a total strain percent at ultimate failure of the part). The static strength data is known for most materials. As an example, to cross-check whether the part 104 can withstand the proof load, a critical geometric component of the part 104 is first determined, and next, formulas to calculate load tolerances for different failure modes of that geometry are identified. If failure mode tolerances are greater than the proof load, the part 104 can handle the proof load. Methods for calculating load capacity of different geometries can be identified by reference to literature or lookup tables.

In one example, the capability testing can include calculating a material ratio of the part 104 as the critical fracture toughness over the threshold stress-intensity factor, calculating a load ratio of the part 104 as a limit load on the part 104 over the operational load, and based on the load ratio being greater than the material ratio, the proof load can be applied to the part 104. A limit load is typically determining during testing, and here, the part 104 should be able to withstand the proof load based on materials used during manufacturing, for example. Thus, to determine whether a candidate part may be cleared for fatigue using the proofing method, the ratio of the limit load on the part over its operational load can be calculated and this load ratio can then be compared to the ratio of the printed material's critical stress-intensity factor over its threshold stress-intensity factor. If the load ratio is greater than the material's stress-intensity factor ratio, the part will likely be a good candidate for applying the proofing method. Otherwise, a more complete analysis may be performed or traditional non-destructive inspection (NDI) methods can be considered.

Further factors can be considered when determined whether the proof load testing is applicable for a specific part. For example, the proof load tends to be higher than the operational load, however. As a result, the proof loading technique is useful for parts that are subject to high static loads but relatively low operational (fatigue) loads. High static loads and low operational loads are typical of parts sized by jam and failure conditions, for example. Certain aircraft systems, such as high-lift actuators and flight controls, fall into this category. High-lift actuator housings and flight control bellcranks are often of cast construction, which makes the parts good candidates for substitution with metal additively-manufactured spares.

As another example, the capability testing can include determining a thickness of a fatigue-critical section of the part, and based on the thickness of a fatigue-critical section of the part being less than a threshold thickness, the proof load can be applied to the part. The fatigue-critical section of the part can vary from part to part, but may generally include a movable section of the part that will be subject to large forces when in use. Thick wall and relatively high-toughness materials do not always result in high fracture toughness, but rather, the fracture toughness may decrease with increasing thickness. Thin sections of a part will tend to experience a plane-stress condition while thicker sections will experience a plane-strain condition at their mid-surface. Since fracture toughness levels off with sections of a half-inch thickness, these structures will have lower proofing loads than more slender sections. The threshold stress-intensity factor is not affected by the thickness of a section. Thus, it has been found that for thinner parts, a higher proof load is needed for application than for thicker parts during compliance testing.

As another example, the capability testing can consider a direction of proof-load application. The direction of loading can change significantly for certain mechanisms, such as bellcranks. In other mechanisms, such as high-lift actuator housings, the loading direction remains largely fixed. In cases when there are large changes in loading direction, the two limits of operational loading should be considered when applying the proof load.

Following, at block 142, it is determined if positive margins result from the capability testing. A positive margin may result as a form of a binary testing. For example, it can be determined as a yes/no decision.

Based on a determination that the part 104 can withstand the proof load, the proof load can be applied to the part 104 during a compliance (e.g. acceptance) test of the part 104, as shown at block 144. The proof load may be applied, for example, using the test equipment 108. The proof load will cause the part 104 to fracture, when applied to the part 104, based on presence of the internal flaw in the part 104 that is of a threshold size at which the internal flaw would cause cracking and potential part failure when the part 104 is placed under the operational load. Once the proof load is applied, it can be determined whether the part passed the compliance test by analyzing the part for cracks, for example.

Based on a determination that the part 104 cannot withstand the proof load, compliance testing may be performed using a NDI method to detect flaws, as shown at block 146.

Using examples described herein, intention of the proof load is to apply a large enough load to the part 104 to cause any flaws in the part 104 that could grow under operational load to fracture during compliance testing. If a moving part is being analyzed, the proof load should be found for an extreme position(s) of movement of the part 104.

Figure 3:
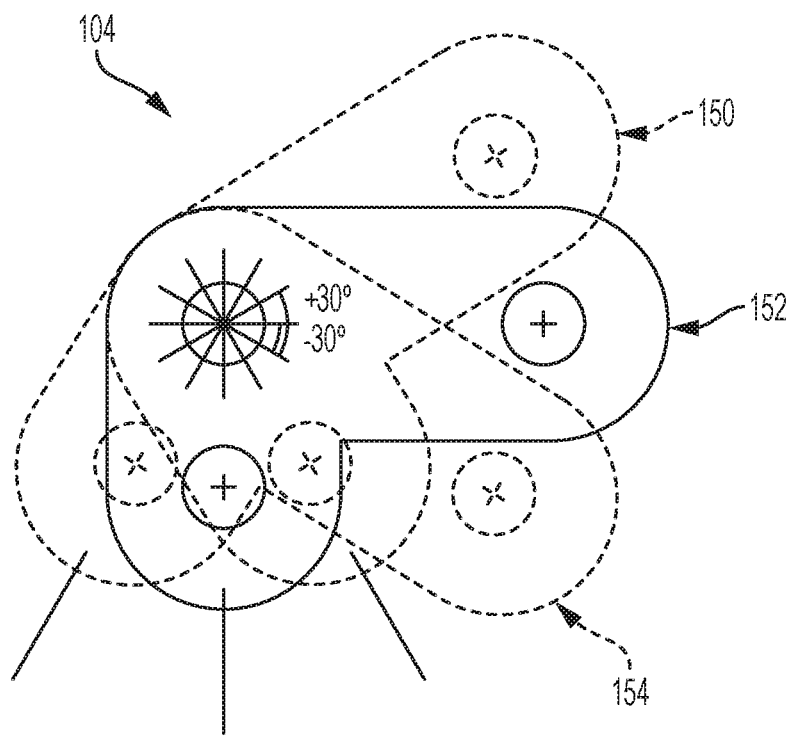
FIG. 3 illustrates an example part for compliance testing and determination of positions of movement of the part for testing, according to an example implementation.

FIG. 3 illustrates an example part for compliance testing and determination of positions of movement of the part for testing, according to an example implementation. The part shown in FIG. 3 is a bellcrank that has a range of motion shown by the dotted lines and the part be capable of being positioned at those positions. For example, at position 150 the bellcrank is at a maximum positive deflection, at position 152 the bellcrank is at a neutral position, and at position 154 the bellcrank is at a maximum negative deflection. Thus, when the part undergoing compliance test includes one or more moving components with a range of movement, the part can be positioned in a substantially maximum position in the range of movement, and then the proof load can be applied to the part in the substantially maximum position. Using the bellcrank shown in FIG. 3, this may be at position 150 and/or 154. Such testing is beneficial because it is typically at these extreme positions that a maximum operational load on the part will occur.

Figure 4:
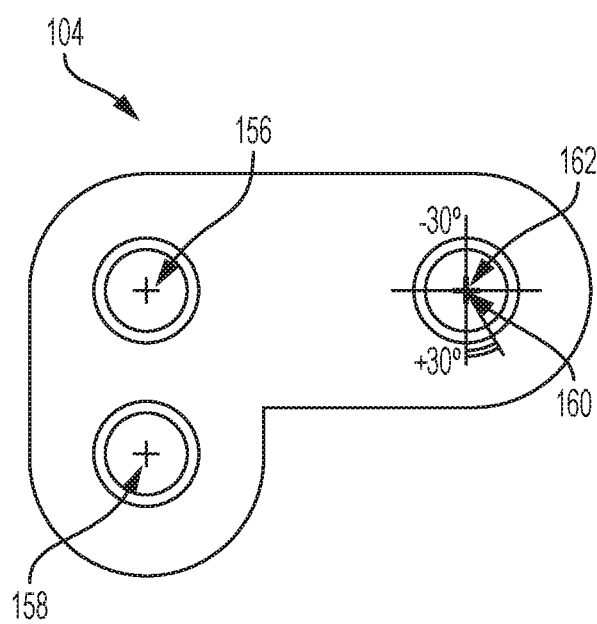
FIG. 4 illustrates the part being placed into position for compliance testing, according to an example implementation.

FIG. 4 illustrates the part 104 being placed into position for compliance testing, according to an example implementation. After the position of the part 104 is determined for testing, the part 104 is then fixed at joints to the test equipment 108 and the proof load is applied at critical joint(s). As shown in FIG. 4, the part 104 is fixed using pins 156 and 158 to the test equipment 108, and the proof load for maximum positive deflection (e.g., position 150) can be applied at a positive 30° angle as shown by arrow 160. Then, the proof load for maximum negative deflection (e.g., position 154) can be applied at a negative 30° angle as shown by arrow 162.

During testing, a stiffness of the test equipment 108 attachments can be made to be similar to a stiffness of structures on the vehicle or aircraft in which the part 104 will be installed.

Note that application of the proof load for the critical positions and orientations of the part 104 will verify whether a flaw of a critical size exists within the part 104. If the part 104 survives the proof load application, this indicates that no flaw large enough to grow at operational load exists within the part 104. If the part 104 fractures upon proof load application, this indicates that the part 104 contained a flaw within it large enough to grow at the operational load.

For compliance testing, if the proof load required by Equation (1) above is greater than an original design limit load of the part, this proof load effectively becomes a new limit load for the part. This is because every part produced will experience the proof load during compliance testing. The new ultimate load for the part will then, in turn, be driven by the proof load. Following, if a new, higher, ultimate load is forced by the proof load, a prototype part should be produced and subjected to ultimate testing as a part of the part's strength qualification.

As mentioned above, a print direction of the part has been found to have an effect on fracture toughness but not on the threshold stress-intensity factor. Since the required proof load in order to clear a component to fatigue in Equation (1) is proportional to the ratio of fracture toughness to the threshold stress-intensity factor, the print direction has a potential to reduce a required proof load when other conditions are met. First, proof loads at a fracture-critical feature should not change much in direction during operation of the part. If a large change in angle of load application occurs during routine use, the applied proof load may not have been sufficient to ensure that a flaw oriented towards a load application that was not tested for does not exist. Second, the print direction needs to be specified in order to make use of this feature. This may not always be possible, as the part may require a certain print orientation in order to ensure that it can be fabricated. Finally, a geometry of the loading should be considered. If a radially symmetric part is subject to a torque, for example, lugs at different clocking positions may have different critical fracture toughness values given their orientation.

Figure 5:
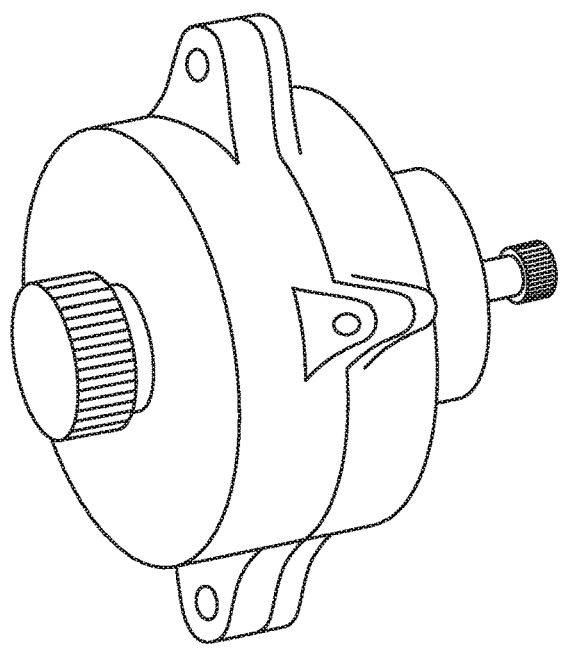
FIG. 5 shows an example flap actuator that is used to roll out and retract wing flaps on an aircraft, according to an example implementation.

An example proof load assessment was performed in an additively manufactured part. FIG. 5 shows an example flap actuator that is used to roll out and retract wing flaps on an aircraft, according to an example implementation. The actuator housing has historically been made of aluminum castings, and these castings are subject to radiographic inspections for quality control. Radiographic inspection of an additively manufactured metal part can be difficult due to the rough surface finish of an as-printed surface creating a haze on the X-ray image, and thus, the proof load method has the potential to be useful. For the proof load assessment, the printed aluminum was assumed to have the same static properties as its casted counterpart.

Figure 6:
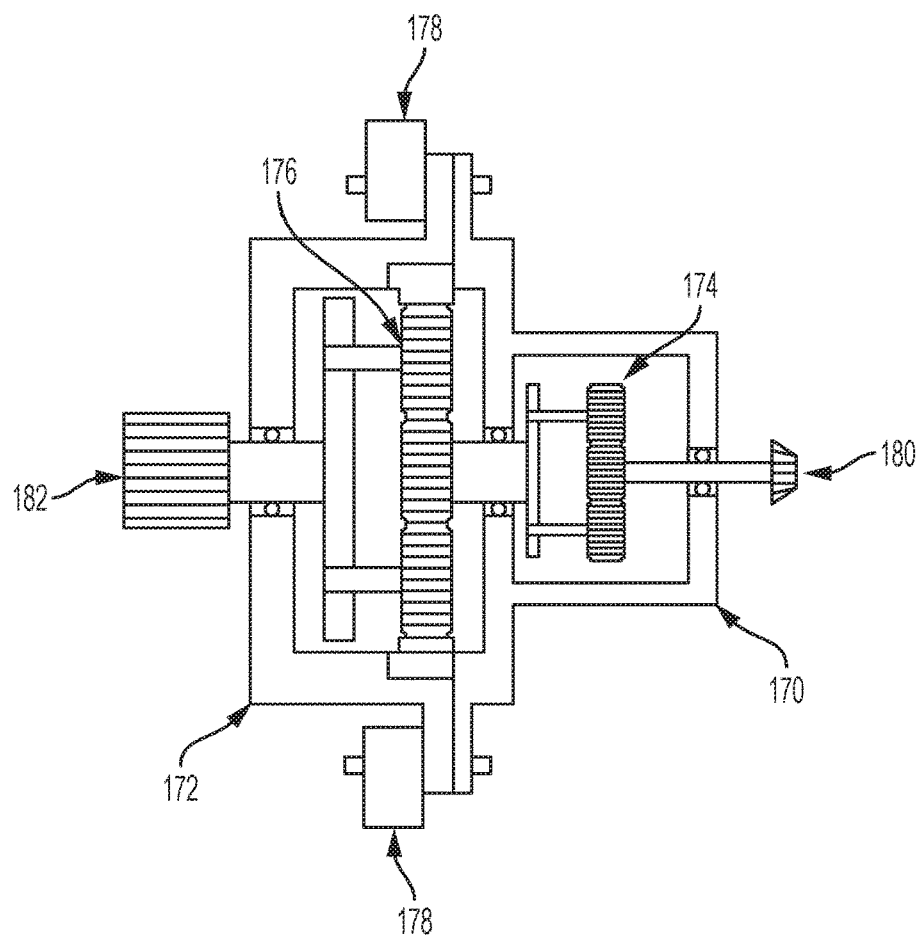
FIG. 6 shows a cross-sectional view of the flap actuator, according to an example implementation.

FIG. 6 shows a cross-sectional view of the flap actuator, according to an example implementation. A typical flap actuator includes a housing of two parts (e.g., input housing 170 and output housing 172) pinned together around a two-stage planetary gear box 174 and 176. The flap actuator is connected to an airframe 178 by four pins. The input housing 170 on the right side is connected to a torque limiter through an input gear 180, and the output housing 172 on the left side is connected to an elbow joint through output spline 182 that rolls out and retracts wing flaps. Each flap has two flap actuators for the inboard and outboard flap tracks.

In this example, a focus is on the output housing 172, which sees significantly higher torques than the input housing 170. For example, a scenario in which the flap actuator housing would experience a greatest loading is a failure case during a flap retraction. During this operation, the inboard actuator experiences a jam internal to the gear box. At the same time, the torque limiter for the outboard actuator fails. Because of this, the inboard side of the flap fails to retract with the outboard side and the outboard actuator is allowed to continue to try to retract the flap. Skew sensors on the elbow joints would arrest the retraction once detected, but the flap actuator should be capable of absorbing the load until the skew sensors trigger. The outboard actuator causes the inboard side of the flap to pull against the inboard actuator. Since the jam is internal to the gear box, the load will be reacted in lug of the housing that hold the actuator to the airframe.

Figure 7:
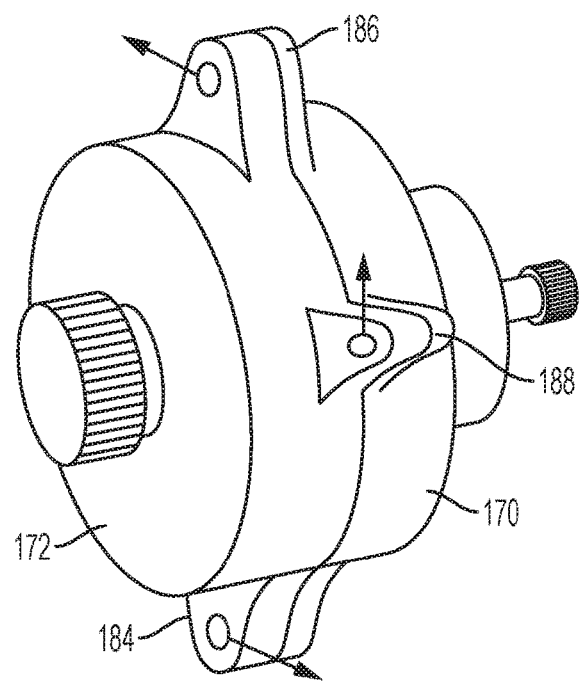
FIG. 7 illustrates the example flap actuator with loading vectors on housing lugs, according to an example implementation.

FIG. 7 illustrates the example flap actuator with loading vectors on housing lugs, according to an example implementation. Thus, in the failure scenario explained above, each of housing lugs 184, 186, and 188 will experience a loading vector in a different direction, as shown. The flap actuator may include four housing lugs, with a fourth lug on an opposite side of the flap actuator not shown in FIG. 7.

Figure 8:
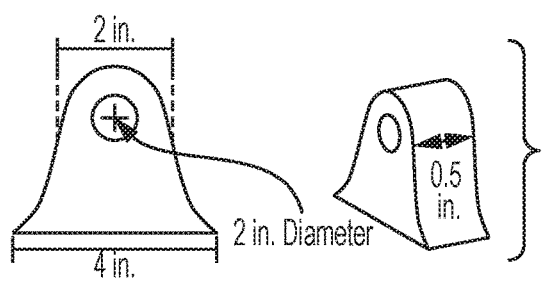
FIG. 8 illustrates example dimensions for each lug of the output housing, according to an example implementation.

FIG. 8 illustrates example dimensions for each lug of the output housing 172, according to an example implementation. The dimensions include 4 inches wide at the base and 2 inches wide at the top by 0.5 inches depth. For this example, the jam torque is 50,000 lbf-in and the operating torque is 6,000 lbf-in. These torques are shared between the four lugs, and the lug pin is five inches from a center of the flap actuator, vertically oriented as compared with the horizontal dimensions shown in FIG. 8. Based on these values, an operating load can be found for one of the lugs using Equations (9)-(11).

$$\tau_{op} = P_{op} * 4 * (5 \text{ in}) \qquad \text{Equation (9)}$$

$$P_{op} = \frac{(6,000 \text{ lbf} - \text{in})}{(4 * (5 \text{ in}))} \qquad \text{Equation (10)}$$

$$P_{op} = 3000 \text{ lbf} \qquad \text{Equation (11)}$$

An assumed threshold stress-intensity factor for printed aluminum is shown in Equation (12) below.

$$K_{th} = 1.5 \text{ ksi}\sqrt{\text{in}} \qquad \text{Equation (12)}$$

Using a fracture toughness versus thickness curve for cast aluminum, which is known, a critical stress intensity factor for the output housing lug thickness is shown in Equation (13).

$$K_c = 15 \text{ ksi}\sqrt{\text{in}} \qquad \text{Equation (13)}$$

Given these values, Equation (1) can be used to find a proof load for the output housing. Equations (14)-(15) show results for this specific case.

$$P_{proof} = \left(\frac{15 \text{ ksi}\sqrt{\text{in}}}{1.5 \text{ ksi}\sqrt{\text{in}}}\right) * (300 \text{ lbf}) \qquad \text{Equation (14)}$$

$$P_{proof} = 3,000 \text{ lbf} \qquad \text{Equation (15)}$$

Based on these results, the output housing would need to be subjected to a 3,000 pound load at one of the lugs. If the output housing does not fracture, then the part does not have a crack large enough to grow during operation.

A comparison of the total torque from the proof load results in 60,000 lbf-in. This is greater than the jam torque of 50,000 lbf-in. As a result of this, the ultimate load that should be applied during the part's qualification testing will be driven by the proof torque on the actuator rather than the jam torque. Ultimate loads are typically 1.5× the limit load on a component.

The printed material was assumed to have a yield strength of 28 ksi, an ultimate tensile strength of 38 ksi, a bearing ultimate strength of 65 ksi, and 3% elongation, identical to its casted counterpart. Applying the corresponding limit load of 3,000 lbf and the ultimate load of 4,500 lbf on the attachment lugs of the actuator returns a limit margin of safety of +36% and an ultimate margin of safety of +51% on the attachment lugs of the actuator.

In this example, for the actuator housing to have full load-carrying capability, the actuator housing would need to be printed perpendicular to the loading vector, for example, since the print direction for an additive manufactured replacement part affects its loading capability given a certain loading configuration.

Figure 9:
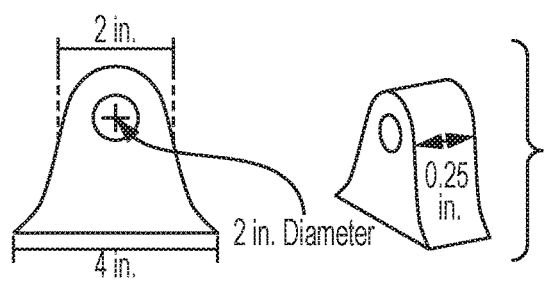
FIG. 9 illustrates example dimensions for each lug of the output housing using a smaller design, according to an example implementation.

A thickness of the critical section of the housing lug can be significant in determining the proof load on the part. Suppose that a similar design of flap actuator is used on an aircraft, but is half as large as the design shown in FIGS. 5-8. The flap drive is scaled down accordingly, generating only half the jam torque. The internal gearing of the part remains unchanged from the previous example, but a thickness of the housing is reduced to save weight. FIG. 9 illustrates example dimensions for each lug of the output housing 172 using the smaller design, according to an example implementation. Referring to FIG. 9, and given that the output housing lug is 0.25 inches thick (with 4 inches wide at the base and 2 inches wide at the top), the fracture toughness of the material increases to 35 ksi√in.

As described earlier, a smaller aircraft in this example has half of the flap drive output torque than in the previous example. An operational load on the output housing is estimated in Equations (16)-(18) below.

$$P_{op\_small} = \frac{P_{op}}{2} \quad \text{Equation (16)}$$

$$P_{op\_small} = \frac{300 \, lbf}{2} \quad \text{Equation (17)}$$

$$P_{op\_small} = 150 \, lbf \quad \text{Equation (18)}$$

The threshold stress-intensity of the more slender output housing lug is the same as that of the output housing lug from the previous example. The fracture toughness, however, is greater, as shown in Equation (19) below.

$$K_{c\_small} = 32.5 \, ksi\sqrt{in} \quad \text{Equation (19)}$$

A required proof load for the more slender output housing lug is given below in Equations (20)-(21).

$$P_{proof\_small} = \frac{(32.5 \, ksi\sqrt{in})}{(1.5 \, ksi\sqrt{in})} * (150 \, lbf) \quad \text{Equation (20)}$$

$$P_{proof\_small} = 3{,}250 \, lbf \quad \text{Equation (21)}$$

The proof load on the more slender output housing lug has increased 8% over the proof load on the output housing lug from the previous example. However, the cross-sectional area of the lug has decreased to 50% of the lug in the previous example. This results in the proof load application generating a margin of safety of −37% at limit load and −30% at ultimate load. The proofing method would therefore not be as useful for the more slender lug on the actuator in this example, even though the operational load on the actuator has scaled down proportionally.

The examples above indicate methods for identifying a proof load that will cause any crack large enough to grow under operational load in a part to fracture upon proof load application. This makes the suggested proofing of a component a good candidate for an acceptance test procedure, as it ensures that the part does not contain a flaw large enough to grow. This method requires the threshold stress-intensity factor, critical stress-intensity factor, and operational load on the part. Tests can be performed to obtain the critical and threshold stress intensity factors for the printed metal in the print and printer-bed directions. Proofing metal additive manufacturing parts is of interest because spare castings can be difficult to source for ageing aircraft platforms, and metal additive manufacturing is an efficient method to source replacements assuming that only a small production run of spares is required.

Figure 10:
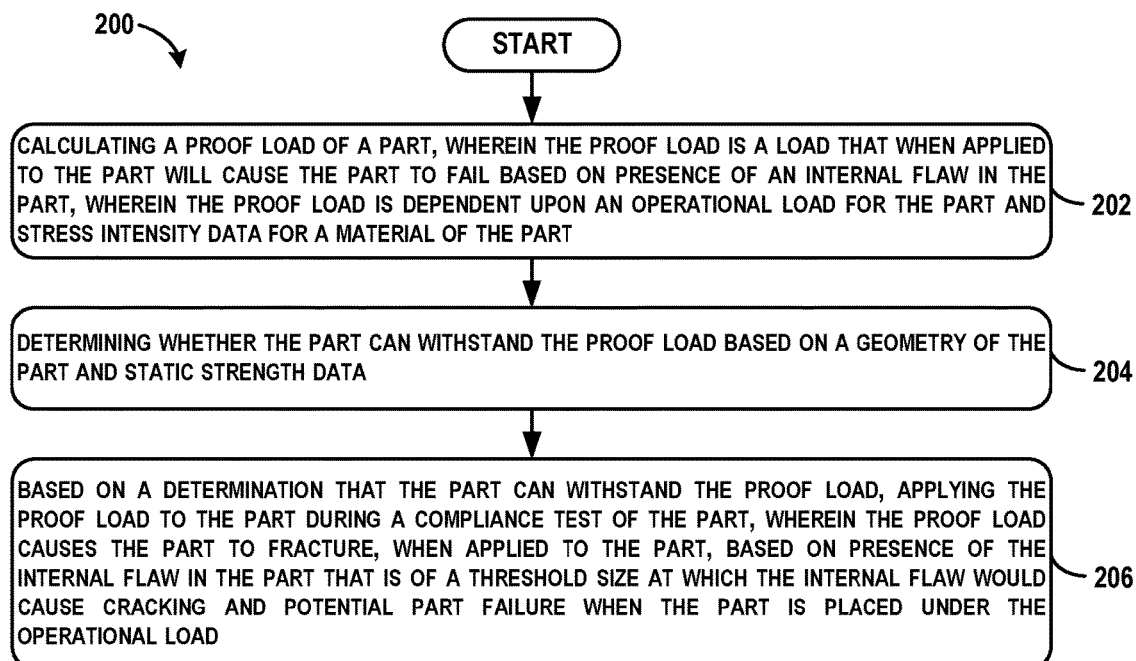
FIG. 10 shows a flowchart of an example method for identifying an internal flaw in the part produced using additive manufacturing, according to an example implementation.

FIG. 10 shows a flowchart of an example method 200 for identifying an internal flaw in the part 104 produced using additive manufacturing, according to an example implementation. Method 200 shown in FIG. 10 presents an example of a method that could be used with the work environment 100 or system 102 shown in FIG. 1 or with components of the work environment 100, for example. Further, devices or systems may be used or configured to perform logical functions presented in FIG. 10. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 200 may include one or more operations, functions, or actions as illustrated by one or more of blocks 202-206. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. In this regard, some or each block or portions of some or each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block or portions of each block in FIG. 10, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

At block 202, the method 200 includes calculating a proof load of the part 104. The proof load is a load that when applied to the part 104 will cause the part 104 to fail based on presence of an internal flaw in the part 104, and the proof load is dependent upon an operational load for the part 104 and stress intensity data for a material of the part 104.

Figure 11:
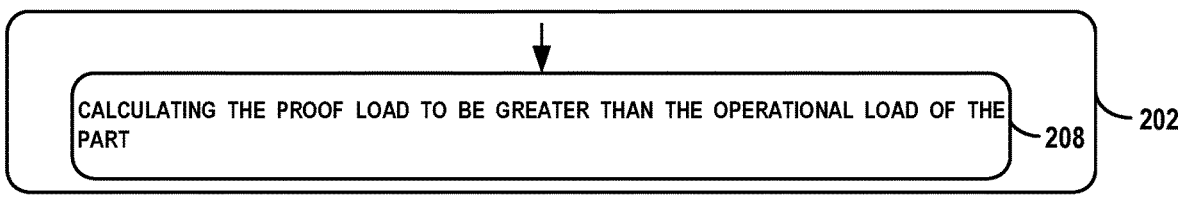
FIG. 11 shows a flowchart of an example method for calculating the proof load of the part of FIG. 10, according to an example implementation.

FIG. 11 shows a flowchart of an example method for calculating the proof load of the part as shown in block 202 of FIG. 10, according to an example implementation. At block 208, functions include calculating the proof load to be greater than the operational load of the part 104.

Figure 12:
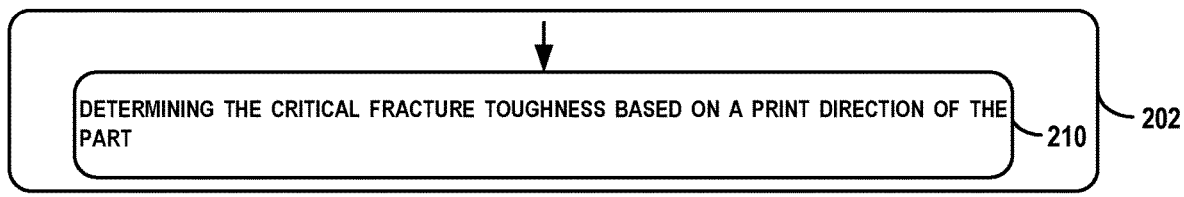
FIG. 12 shows another flowchart of an example method for calculating the proof load of the part of FIG. 10, according to an example implementation.

FIG. 12 shows another flowchart of an example method for calculating the proof load of the part as shown in block 202 of FIG. 10, according to an example implementation. At block 210, functions include determining the critical fracture toughness based on a print direction of the part.

Figure 13:
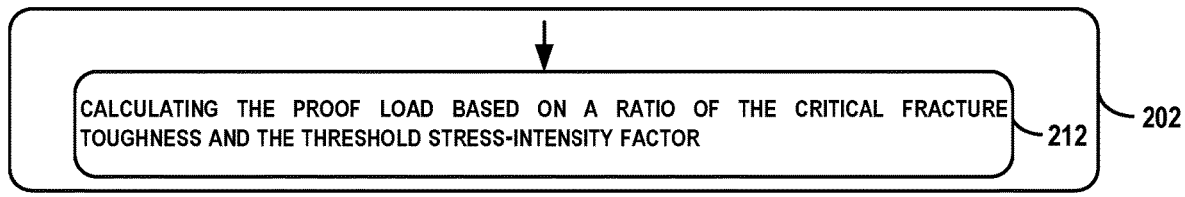
FIG. 13 shows another flowchart of an example method for calculating the proof load of the part of FIG. 10, according to an example implementation.

FIG. 13 shows another flowchart of an example method for calculating the proof load of the part as shown in block 202 of FIG. 10, according to an example implementation. At block 212, functions include calculating the proof load based on a ratio of the critical fracture toughness and the threshold stress-intensity factor.

Figure 14:
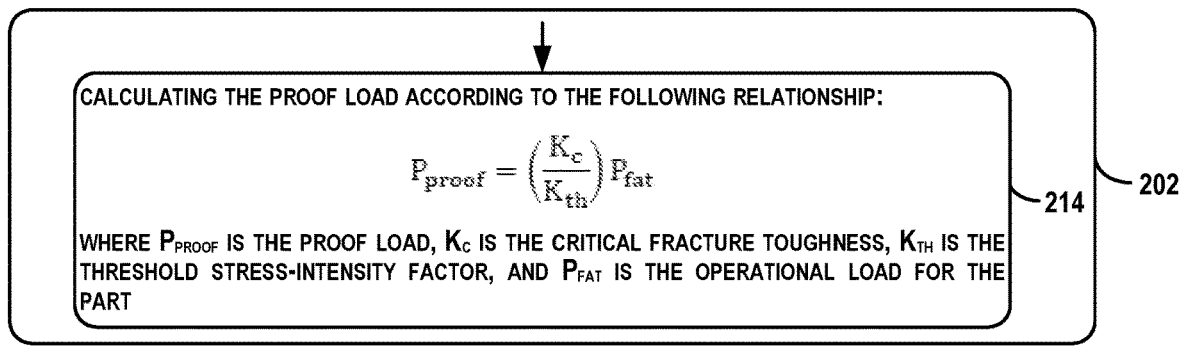
FIG. 14 shows a flowchart of an example method for calculating the proof load of the part of FIG. 10, according to an example implementation.

FIG. 14 shows a flowchart of an example method for calculating the proof load of the part as shown in block 202 of FIG. 10, according to an example implementation. At block 214, functions include calculating the proof load according to the following relationship:

$$P_{proof} = \left(\frac{K_c}{K_{th}}\right) P_{fat}$$

where $P_{proof}$ is the proof load, $K_c$ is the critical fracture toughness, $K_{th}$ is the threshold stress-intensity factor, and $P_{fat}$ is the operational load for the part.

Returning to FIG. 10, at block 204, the method 200 includes determining whether the part 104 can withstand the proof load based on a geometry of the part 104 and static strength data.

At block 206, the method 200 includes based on a determination that the part can withstand the proof load, applying the proof load to the part during a compliance test of the part, and the proof load causes the part 104 to fracture, when applied to the part 104, based on presence of the internal flaw in the part 104 that is of a threshold size at which the internal flaw would cause cracking and potential part failure when the part 104 is placed under the operational load.

Figure 15:
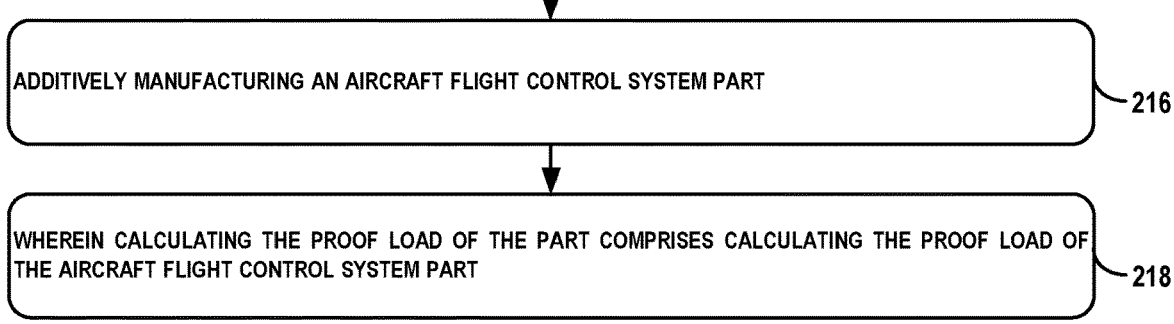
FIG. 15 shows a flowchart of an example method for use with the method of FIG. 10, according to an example implementation.

FIG. 15 shows a flowchart of an example method for use with the method 200 of FIG. 10, according to an example implementation. At block 216, functions include additively manufacturing an aircraft flight control system part, and at block 218, functions include calculating the proof load of the aircraft flight control system part.

Figure 16:
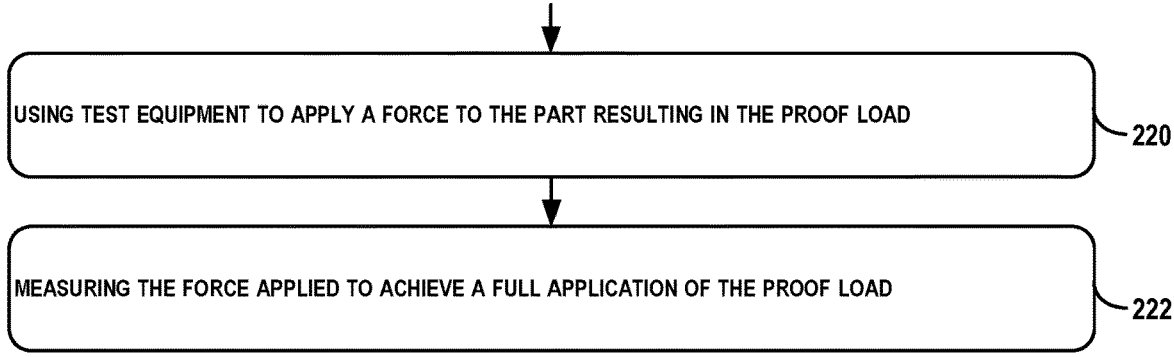
FIG. 16 shows a flowchart of an example method for use with the method of FIG. 10, according to an example implementation.

FIG. 16 shows a flowchart of an example method for use with the method 200 of FIG. 10, according to an example implementation. At block 220, functions include using the test equipment 108 to apply a force to the part resulting in the proof load, and at block 222, functions include measuring the force applied to achieve a full application of the proof load.

Figure 17:
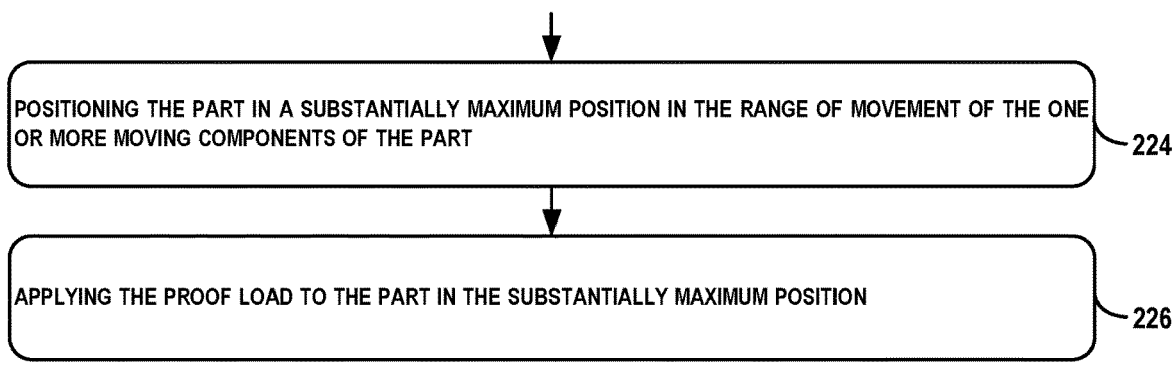
FIG. 17 shows a flowchart of an example method for use with the method of FIG. 10, according to an example implementation.

FIG. 17 shows a flowchart of an example method for use with the method 200 of FIG. 10, according to an example implementation. At block 224, functions include positioning the part in a substantially maximum position in the range of movement of the one or more moving components of the part, and at block 226, functions include applying the proof load to the part in the substantially maximum position.

FIG. 18 shows a flowchart of an example method for use with the method 200 of FIG. 10, according to an example implementation. At block 228, functions include performing one or more tests to obtain the critical fracture toughness and the threshold stress-intensity factor of the material for the part in x, y, and z directions.

FIG. 19 shows a flowchart of an example method for determining whether the part can withstand the proof load based on the geometry of the part and the static strength data, as shown in block 204 of FIG. 10, according to an example implementation. At block 230, functions include identifying the static strength data including tensile strength (Ftu), yield strength (Fty), yield bearing strength (Fbru), and percent elongation of the material of the part.

FIG. 20 shows another flowchart of an example method for determining whether the part can withstand the proof load based on the geometry of the part and the static strength data, as shown in block 204 of FIG. 10, according to an example implementation. At block 232, functions include performing a simulation resulting in a binary decision. For example, binary decisions can include results such as 'pass' or 'fail', 'positive margin exists' or 'positive margin does not exist', 'go' or 'stop', 'yes' or 'no', 'enable' or 'disable', and 'on' or 'off'.

FIG. 21 shows another flowchart of an example method for use with the method 200 of FIG. 10, according to an example implementation. At block 234, functions include calculating a material ratio of the part as the critical fracture toughness over the threshold stress-intensity factor, at block 236, functions include calculating a load ratio of the part as a limit load on the part over the operational load, and at block 238, functions include, based on the load ratio being greater than the material ratio, applying the proof load to the part.

FIG. 22 shows another flowchart of an example method for use with the method 200 of FIG. 10, according to an example implementation. At block 240, functions include determining a thickness of a fatigue-critical section of the part, and at block 242, functions include based on the thickness of a fatigue-critical section of the part being less than a threshold thickness, applying the proof load to the part.

FIG. 23 shows another flowchart of an example method for use with the method 200 of FIG. 10, according to an example implementation. At block 244, functions include using a non-destructive inspection method during the compliance test of the part.

Further enhancements, functions, or operations may be performed in addition to the method 200 of FIG. 10. In one example, an operational load of the casted part can be retrieved from a database per part specification or empirical testing of the parts, and a material having a strength necessary to satisfy the operational loading can be specifically selected for use to additively manufacture the replacement part. Following, the replacement part can be additively manufactured, and the proof load may be calculated as described herein for compliance testing.

Additional or alternative enhancements, functions, or operations to be performed to the method 200 of FIG. 10 also include analyzing outputs of the application of the proof load on the additively manufactured part. For example, based on an outcome of the compliance test, it may be determined that a thickness of the part should be altered (e.g., make it thinner or thicker), or a different material should be used for printing. Thus, as shown in FIG. 1, the test equipment may have a feedback loop to the system 102 to provide data of the test useful for making changes to part production. Further, in instances where the part failed the test, the additive manufacturing device 106 may be checked for errors in operation or flaws itself that caused errors in production. As a result, the proof loading testing procedure can become an iterative process to arrive at a part produced in an optimal manner (e.g., thickness, design, material) all controlled by the system 102.

Still further, the proof load calculation techniques described herein are useful for methods for determining an appropriate acceptance or compliance test for use on a specific part. As mentioned above, with respect to FIG. 2, in instances in which the part is not compatible with the proof load testing, NDI testing techniques can be recommend for use.

Examples described herein further provide technological improvements that are particular to solving issues of ensuring that additive manufactured parts, and particularly additive manufactured metal parts, will not crack due to fatigue loading over a service life of the part. This can address technical problems, such as streamlining certification process for additive manufactured parts to show that the part will not be prone to fatigue failure once the part passes the acceptance test procedure. A traditional proof load is simply taken as 1.5 times a limit load, but this may not always guarantee that the part does not include internal flaws, especially for additive manufactured parts. Thus, examples herein utilize fracture mechanics to generate a proof load capable of sufficiently testing the part.

The proof load calculation and application processes described herein include a non-conventional testing procedure (e.g., not used for casted parts) that can sufficiently test additive manufactured parts manner to reduce errors in compliance testing. Proof loading can thus be used to certify or qualify a part produced with additive manufacturing to provide a greater guarantee that the part will be operative during the service life of the part as compared to NDI testing.

Using a load application for the Acceptance Test Procedure alleviates a requirement for non-destructive inspection (NDI) of additive manufactured parts so that internal flaws, which can be difficult to detect via X-ray inspection due to surface roughness of the parts, may be more easily detected. Any part that survives the test should therefore not contain any flaws that might cause the part to fail in fatigue. While NDI can detect a presence of a crack in some instances, the load application method captures flaws of sufficient size and in an orientation that would adversely affect the service life of a part.

By the term "substantially" and "about" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination or any sub-combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A method for identifying an internal flaw in a part produced using additive manufacturing, the method comprising:
   calculating a proof load of the part, wherein the proof load is a load that when applied to the part will cause the part to fail based on presence of the internal flaw in the part, wherein the proof load is dependent upon (i) an operational load for the part obtained from prior usage of non-additive manufacturing parts and (ii) stress intensity data for a material of the part, wherein the stress intensity data for the material of the part comprises a critical fracture toughness and a threshold stress-intensity factor of the material for the part, wherein the critical fracture toughness is based on a print direction of the part;
   calculating a material ratio of the part as the critical fracture toughness over the threshold stress-intensity factor;
   calculating a load ratio of the part as a limit load on the part over the operational load, wherein the limit load is a highest load expected to be experienced by the part in service; and
   based on the load ratio being greater than the material ratio, applying the proof load to the part during a compliance test of the part, wherein the proof load causes the part to fracture, when applied to the part, based on presence of the internal flaw in the part that is of a threshold size at which the internal flaw would cause cracking and potential part failure when the part is placed under the operational load.

2. The method of claim 1, wherein calculating the proof load of the part comprises:
   calculating the proof load to be greater than the operational load of the part.

3. The method of claim 1, wherein calculating the proof load of the part comprises:
   calculating the proof load according to the following relationship:

$$P_{proof} = \left(\frac{K_c}{K_{th}}\right) P_{fat}$$

where $P_{proof}$ is the proof load, $K_c$ is the critical fracture toughness, $K_{th}$ is the threshold stress-intensity factor, and $P_{fat}$ is the operational load for the part.

4. The method of claim 1, further comprising:
   additively manufacturing an aircraft flight control system part; and
   wherein calculating the proof load of the part comprises calculating the proof load of the aircraft flight control system part.

5. The method of claim 1, wherein applying the proof load to the part comprises:
   using test equipment to apply a force to the part resulting in the proof load; and measuring the force applied to achieve a full application of the proof load.

6. The method of claim 1, wherein the part comprises one or more moving components with a range of movement, and wherein the method further comprises:
positioning the part in a substantially maximum position in the range of movement of the one or more moving components of the part; and
applying the proof load to the part in the substantially maximum position.

7. The method of claim 1, wherein the method further comprises:
performing one or more tests to obtain the critical fracture toughness and the threshold stress-intensity factor of the material for the part in x, y, and z directions.

8. The method of claim 1, further comprising determining whether the part can withstand the proof load based on the geometry of the part and the static strength data by:
identifying the static strength data comprising tensile strength (Ftu), yield strength (Fty), yield bearing strength (Fbru), and percent elongation of the material of the part.

9. The method of claim 8, wherein determining whether the part can withstand the proof load based on the geometry of the part and the static strength data comprises:
performing a simulation resulting in a binary decision.

10. The method of claim 1, further comprising:
determining a thickness of a fatigue-critical section of the part; and
based on the thickness of the fatigue-critical section of the part being less than a threshold thickness, applying the proof load to the part.

11. The method of claim 1, further comprising based on a determination that the part cannot withstand the proof load, the method further comprising:
using a non-destructive inspection method during the compliance test of the part.

12. A system for identifying an internal flaw in a part produced using additive manufacturing, the system comprising:
one or more processors; and
a non-transitory computer readable storage medium having stored therein instructions, that when executed by the one or more processors, causes the one or more processors to perform functions comprising:
calculating a proof load of the part, wherein the proof load is a load that when applied to the part will cause the part to fail based on presence of the internal flaw in the part, wherein the proof load is dependent upon (i) an operational load for the part obtained from prior usage of non-additive manufacturing parts and (ii) stress intensity data for a material of the part, wherein the stress intensity data for the material of the part comprises a critical fracture toughness and a threshold stress-intensity factor of the material for the part, wherein the critical fracture toughness is based on a print direction of the part;
calculating a material ratio of the part as the critical fracture toughness over the threshold stress-intensity factor;
calculating a load ratio of the part as a limit load on the part over the operational load, wherein the limit load is a highest load expected to be experienced by the part in service; and
based on the load ratio being greater than the material ratio, causing the proof load to be applied to the part during a compliance test of the part, wherein the proof load causes the part to fracture, when applied to the part, based on presence of the internal flaw in the part that is of a threshold size at which the internal flaw would cause cracking and potential part failure when the part is placed under the operational load.

13. The system of claim 12, further comprising:
test equipment to apply the proof load to the part during a compliance test of the part.

14. The system of claim 12, wherein calculating the proof load of the part comprises:
calculating the proof load of an additively manufactured part comprising an aircraft flight control system part.

15. A non-transitory computer readable storage medium having stored therein instructions, that when executed by a system comprising one or more processors, causes the system to perform functions comprising:
calculating a proof load of a part produced using additive manufacturing, wherein the proof load is a load that when applied to the part will cause the part to fail based on presence of an internal flaw in the part, wherein the proof load is dependent upon (i) an operational load for the part obtained from prior usage of non-additive manufacturing parts and (ii) stress intensity data for a material of the part, wherein the stress intensity data for the material of the part comprises a critical fracture toughness and a threshold stress-intensity factor of the material for the part, wherein the critical fracture toughness is based on a print direction of the part;
calculating a material ratio of the part as the critical fracture toughness over the threshold stress-intensity factor;
calculating a load ratio of the part as a limit load on the part over the operational load, wherein the limit load is a highest load expected to be experienced by the part in service; and
based on the load ratio being greater than the material ratio, causing the proof load to be applied to the part during a compliance test of the part, wherein the proof load causes the part to fracture, when applied to the part, based on presence of the internal flaw in the part that is of a threshold size at which the internal flaw would cause cracking and potential part failure when the part is placed under the operational load.

16. The non-transitory computer readable storage medium of claim 15, wherein calculating the proof load of the part comprises:
calculating the proof load of an additively manufactured part comprising an aircraft flight control system part.

17. The non-transitory computer readable storage medium of claim 15, wherein calculating the proof load of the part comprises:
calculating the proof load according to the following relationship:

$$P_{proof} = \left(\frac{K_c}{K_{th}}\right) P_{fat}$$

where $P_{proof}$ is the proof load, $K_c$ is the critical fracture toughness, $K_{th}$ is the threshold stress-intensity factor, and $P_{fat}$ is the operational load for the part.

18. The non-transitory computer readable storage medium of claim 15, wherein the functions further comprise:
using test equipment to apply a force to the part resulting in the proof load; and measuring the force applied to achieve a full application of the proof load.

19. The non-transitory computer readable storage medium of claim 15, wherein the part comprises one or more moving components with a range of movement, and wherein the functions further comprise:
   positioning the part in a substantially maximum position in the range of movement of the one or more moving components of the part; and
   applying the proof load to the part in the substantially maximum position.

20. The non-transitory computer readable storage medium of claim 15, wherein functions further comprise:
   performing one or more tests to obtain the critical fracture toughness and the threshold stress-intensity factor of the material for the part in x, y, and z directions.

\* \* \* \* \*